(12) United States Patent
Vollbrecht et al.

(10) Patent No.: US 8,435,197 B2
(45) Date of Patent: May 7, 2013

(54) KNEE-JOINT ORTHOSIS

(75) Inventors: Matthias Vollbrecht, Herzberg am Herz (DE); Gert-Peter Brüggemann, Köln (DE); Andreas Gösele-Koppenburg, Lörrach (DE); Raymond Best, Stuttgart (DE); Andree Ellermann, Ettlingen (DE); Hartmut Semsch, Stuttgart (DE); Alfio Albasini, Riazzino (CH); Christian Liebau, Braunschweig (DE); Wolf Petersen, Berlin (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 192 days.

(21) Appl. No.: 12/961,757

(22) Filed: Dec. 7, 2010

(65) Prior Publication Data
US 2011/0137220 A1 Jun. 9, 2011

(30) Foreign Application Priority Data
Dec. 7, 2009 (DE) .......................... 10 2009 057 700

(51) Int. Cl.
*A61F 5/00* (2006.01)
(52) U.S. Cl.
USPC .............................. 602/23; 602/26
(58) Field of Classification Search ............ 602/16, 602/23–27; 128/882
See application file for complete search history.

(56) References Cited

U.S. PATENT DOCUMENTS

| 3,046,981 | A | * | 7/1962 | Biggs, Jr. et al. | 602/26 |
| 4,407,276 | A | * | 10/1983 | Bledsoe | 602/16 |
| 5,556,374 | A | * | 9/1996 | Grace et al. | 602/26 |
| 5,613,943 | A | * | 3/1997 | Palumbo | 602/62 |
| 5,807,298 | A | | 9/1998 | Palumbo | |
| 7,059,329 | B2 | | 6/2006 | Mason et al. | |
| 7,060,045 | B2 | | 6/2006 | Mason et al. | |

FOREIGN PATENT DOCUMENTS

| DE | 112005000570 T5 | 1/2007 |
| WO | 2004069109 A2 | 8/2004 |
| WO | 2005087149 A1 | 9/2005 |

* cited by examiner

*Primary Examiner* — Michael A. Brown
(74) *Attorney, Agent, or Firm* — Holland and Hart LLP

(57) ABSTRACT

In a knee-joint orthosis for guiding the patella of a patient during the transition from an extended position to a flexed position of the knee joint and vice versa, with a fastening means (I) for fastening to a thigh and a lower leg, with at least one laterally arranged stabilizing element that takes up a flexion of the knee joint and bears on the thigh and lower leg, and with a dimensionally stable guide element (6) that can be held in position by an arrangement of tensioning straps and is arranged to bear laterally on the patella by way of a lateral base part (7) from which medially directed attachments (8) extend proximally and distally of the patella and are secured to strap sections (10, 12) on the orthosis in the area of the thigh and of the lower leg in such a way that a medial tensile force is exerted on the attachments (8).

12 Claims, 2 Drawing Sheets

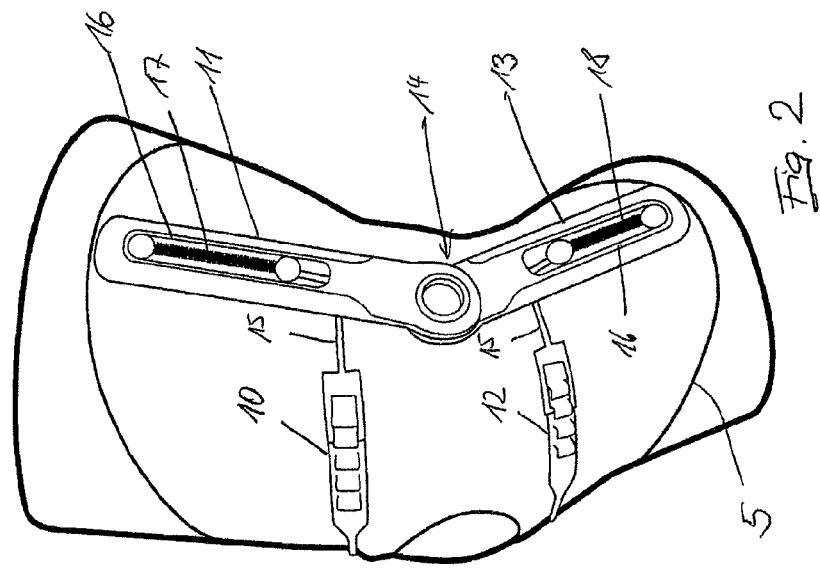
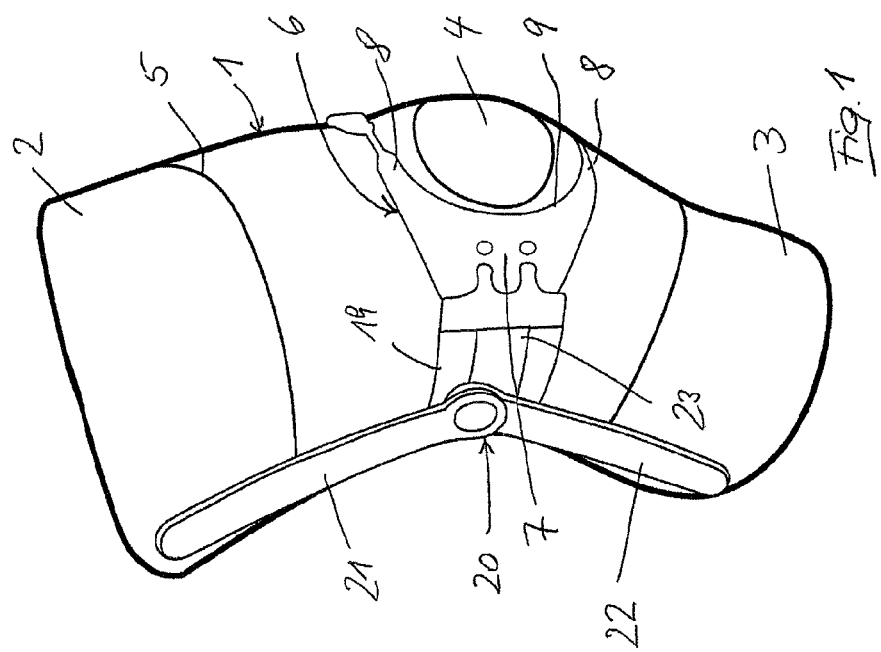

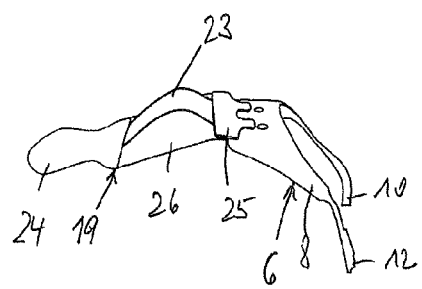 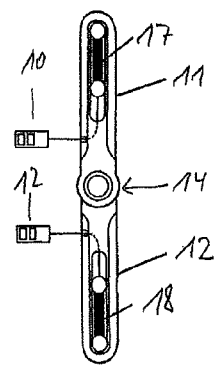
Fig. 3
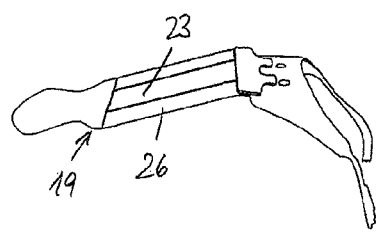 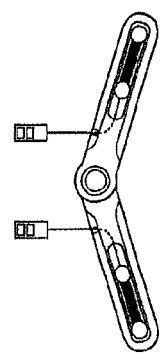
Fig. 4
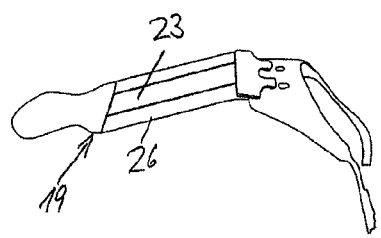 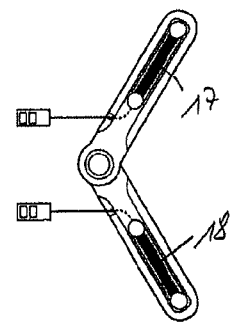
Fig. 5

KNEE-JOINT ORTHOSIS

The invention relates to a knee-joint orthosis for guiding the patella of a patient during the transition from an extended position to a flexed position of the knee joint and vice versa, with a fastening means for fastening to a thigh and a lower leg, with at least one laterally arranged stabilizing element that takes up a flexion of the knee joint and bears on the thigh and lower leg, and with a dimensionally stable guide element that can be held in position by an arrangement of tensioning straps and is arranged to bear laterally on the patella by way of a lateral base part from which medially directed attachments extend proximally and distally of the patella and are secured to strap sections on the orthosis in the area of the thigh and of the lower leg in such a way that a medial tensile force is exerted on the attachments.

Knee-joint orthoses of this kind, which serve to guide the patella (knee cap), are required when, on account of abnormalities or damage, guiding of the patella in the head of the tibia is no longer ensured, especially in the extended position of the knee joint. In this case, movement of the patella then causes painful false positions of the patella, at least during the subsequent flexion of the knee joint. The purpose of a knee-joint orthosis of the type mentioned at the outset is to hold the patella in the correct position when guiding of the patella in the knee joint itself is not ensured across the entire range of flexion of the knee joint.

Such knee-joint orthoses are known from U.S. Pat. No. 7,059,329 B2 and U.S. Pat. No. 7,060,045 B2. They are composed of a shaped thigh part and a shaped lower leg part which, by means of rails connected to them, are pivotable relative to each other about two side hinges. The two attachments of the C-shaped guide element, which partially enclose the patella distally and proximally, are connected by tension straps to the hinge on one side, while the base part of the guide element is connected to the other hinge via a length-adjustable strap. The C-shaped guide element has a padding with which it not only bears laterally from the patella but also acts from above preferably on the lateral margin of the patella, such that the patella is pressed against the knee joint. After some time, the prosthesis wearer finds such pressure on the patella to be uncomfortable. The orthosis is used in conjunction with a sleeve that is made of elastic material and that is pulled over the knee joint, the sleeve having an opening for the patella.

WO 2004/069109 A2 discloses an orthosis that has no hinge rails but instead guides the patella by means of a suitably configured sleeve made of elastic material. A support cushion is located laterally alongside an opening for the patella and is pressed by elastic tensioning straps against the knee joint and the margin of the patella. In this case too, there is a problem of wearing comfort being affected by pressure from above on the patella. In addition, there is no guiding by a lateral hinge with hinge rails.

The object of the present invention is to design a knee-joint orthosis of the type mentioned at the outset in such a way that it ensures reliable guiding of the patella during flexion and extension of the knee joint and has improved properties in respect of wearing comfort.

With a knee-joint orthosis of the type mentioned at the outset, this object is achieved, according to the invention, by the fact that the strap sections are designed with an elasticity, that a laterally directed elastic strap allowing a sideways movement of the base part is connected to the base part, the elasticity of which strap is greater than the elasticity of the strap sections, and that the elasticities of the medially directed strap sections, on the one hand, and of the laterally directed strap, on the other hand, are chosen such that, during a flexion of the hinge from the extended position, it is the laterally directed strap that first stretches at least quite predominantly, and a stretch limiter, provided for the laterally directed strap, is active at a predefined flexion limit angle of the knee joint, such that, for a greater flexion of the knee hinge, it is the medially directed strap sections that stretch at least predominantly.

In the knee-joint orthosis according to the invention, the guide element is held on one side next to the patella, such that it cannot press from above on the patella and, in addition, excessive pressure on the patella can be avoided even at considerable flexion angles. When the knee is flexed from the extended position, the guide element bearing laterally on the patella in the extended state is moved slightly in the direction of the patella until a flexion limit angle is reached. The sideways movement of the guide element caused by the original stretching of the laterally directed strap is at least substantially suppressed by the stretch limiter, such that the elasticity required for the further flexion is made available by the medially directed strap sections. In this way, the position of the guide element relative to the patella does not in practice change any more if the flexion limit angle is exceeded. The laterally directed strap is provided at the height of the hinge, such that it does not move appreciably in the longitudinal direction during flexion or extension of the knee joint.

An embodiment is preferred in which, when the flexion limit angle is exceeded, the flexion limiter completely suppresses any further stretching of the laterally directed strap, such that only the medially directed strap sections stretch.

In a preferred embodiment of the invention, the knee-joint orthosis can be combined with a sleeve of elastic material that is pulled over the patient's leg in the knee area and bears elastically thereon. The sleeve preferably has a front hole through which the patella can protrude, such that a radially inwardly directed pressure through the patella is avoided by the sleeve. The rails of the side hinge can be fastened to the sleeve such that the sleeve functions as a fastening means for the knee-joint orthosis.

The laterally provided stabilizing element, which can take up the flexion movement of the knee joint on the thigh and lower leg, can be a spring element. However, an embodiment is preferred in which a lateral hinge is provided, by means of which a thigh rail bears on the thigh and a lower leg rail bears on the lower leg in such a way that the relative movement of thigh and lower leg is taken up, via a corresponding movement of the rails, as a rotation movement in the hinge. The hinge can be fastened to the sleeve made of elastic material.

The laterally directed strap can then be fastened directly to the laterally arranged hinge. As an alternative to this, the laterally directed strap can also be fastened to the sleeve itself, by being directly fixed by velcro fasteners to the correspondingly configured sleeve. In this case, a length-adjustable design of the laterally directed strap is not needed, whereas in other cases the strap is preferably provided with a length-adjustable section. In this case, the laterally directed strap can have a non-elastic, length-adjustable section and also an elastic section.

The knee-joint orthosis according to the invention can also be designed with a hinge with two rails on the medial aspect, said rails taking up the movement of thigh and lower leg in the area of the knee joint.

The elasticity of the medially directed strap sections can be provided by a material elasticity. In a preferred embodiment, a more precise elasticity of the strap sections can be provided by means of said strap sections being inserted into the support rails and being connected there to a spring element held in a slit of the support rail. The elasticity of the strap section is then provided by the spring element.

The medially directed strap sections are preferably adjustable in length in order to permit adaptation of the knee-joint orthosis to the patient.

The laterally directed strap has a greater elasticity than the medially directed strap sections and is therefore much more easily stretchable. Thus, when the joint is flexed from the extended position, it is first of all the laterally directed strap that stretches quite predominantly. Parallel to the laterally directed strap, the guide element is held for example by a substantially non-elastic stretch-limiting strap which, in the extended state of the joint, has an excess length, such that, in the extended state, no tensile force is exerted on the guide element by the stretch-limiting strap. When, during flexion of the joint as far as the flexion limit angle, the laterally directed elastic strap has stretched to such an extent that the stretch-limiting strap now also exerts a tensile force on the guide element, the at least substantial inelasticity of the stretch-limiting strap prevents further stretching of the laterally directed elastic strap, such that the elasticity required for the further flexion of the joint is provided by the elastic strap sections. Because of the lesser elasticity of the medially directed strap sections compared to the elasticity of the laterally directed strap, a greater resistance is provided against the further flexion movement. Alternatively, the stretch limiter can be incorporated into the laterally directed strap, for example by zigzag seams, woven-in threads or knitted-in threads or the like.

The medially directed strap sections must be fastened to the knee orthosis in such a way that a medial tension is applied to the medially directed attachments of the guide element during the flexion of the knee joint. Accordingly, one of the strap sections is fastened to the thigh and the other of the strap sections is fastened to the lower leg. A direct medial introduction of tension can be effected by means of the strap sections being fastened in the medial area or in the dorsal area. However, fastening in the frontal area is also possible if a corresponding conversion of the strap sections takes place, as a result of which the tensile force directed proximally and distally during flexion is converted into a medially directed tensile force. For this purpose in particular, the strap sections can also be designed, at least in part, with a string shape or wire shape.

The invention is explained in more detail below on the basis of an illustrative embodiment depicted in the drawing, in which:

FIG. 1 shows a perspective view of a knee orthosis according to the invention, obliquely from the lateral direction;

FIG. 2 shows a perspective view of the knee orthosis according to FIG. 1, obliquely from the medial direction;

FIG. 3 shows a schematic view of the guide element with the laterally directed strap and the medially directed strap sections, and of the guide rails of the hinge in the extended state;

FIG. 4 shows a view according to FIG. 3, in a state in which the joint has been flexed about a flexion limit angle;

FIG. 5 shows a view according to FIG. 3, with the joint flexed beyond the flexion limit angle.

FIGS. 1 and 2 are schematic views of a knee-joint orthosis for a patient's right knee joint. The orthosis has a sleeve 1 made of a textile elastic material and designed to be pulled over the knee joint and adapt to the shape of the knee joint. The sleeve forms a thigh section 2 and a lower leg section 3. On its front, the sleeve 1 has an opening 4 through which a patient's patella protrudes when the orthosis is correctly fitted. The sleeve 1 is made up of several pieces of material connected to one another by seams 5.

Lying on the sleeve 1, laterally alongside the opening, there is a dimensionally stable guide element 6 made up of a base part 7, lying laterally alongside the opening 4, and of attachments 8 that are directed medially from the base part 7 and extend above and below the opening 4, such that the guide element 6 is approximately C-shaped. A corresponding C-shaped edge 9 can be curved upward from the base part 7 and, if appropriate, can be provided with padding so as to bear gently on the margin of the patella.

The upper attachment 8 is connected by a strap section 10 to a thigh rail 11, and the lower attachment 8 is connected by a strap section 12 to a lower leg rail 13, of a first hinge 14. The strap sections 10, 12 are adjustable in length and protrude with a string-like end 15 into the rails 11, 13, where they are connected to a spring element 17, 18 guided in a slit 16 of the rails 11, 13. The strap sections 10, 12 are thus made elastic by the spring elements 17, 18, and the material outside the spring elements 17, 18 can be non-elastic, such that the elasticity results only from the elasticity of the spring elements 17, 18.

The base part 7 of the guide element 6 is adjoined laterally by a strap 19 made of an elastic material. The strap 19 provides the connection between the guide element 6 and a second hinge 20, to which the strap 19 is connected at its second end. The second hinge 20 likewise has a thigh rail 21 and a lower leg rail 22, which are both connected to the sleeve 1, for example by being pushed into corresponding pockets of the sleeve 1.

The strap 19 is bridged by a stretch-limiting strap 23, which is made of a non-elastic material and likewise provides a connection between the second hinge 20 and the guide element 6.

It will be seen from FIGS. 3 to 5 that the laterally directed strap 19 is composed of fastening sections 24, 25, between which an elastic section 26 is arranged. The fastening section 24 serves to fasten the strap 19 on the second hinge 20, and the fastening section 25 serves to fasten the strap 19 on the guide element 6. It will be seen from FIG. 3 that the elastic section 26 of the strap 19 is bridged by the stretch-limiting strap 23, which is therefore likewise arranged between the fastening sections 24, 25. The stretch-limiting strap 23 has a greater length than the elastic section 26 in the extended position of the hinge 14, with the result that the stretch-limiting strap 23, because of its excess length, curves upward, as is shown in FIG. 3. It will also be seen from FIG. 3 that, by means of the straps 10, 12, the spring elements 17, 18 are located, in the extended state, in a starting position in which they are unstretched or only slightly stretched.

If the knee joint, and thus the hinge 14, is flexed as far as a flexion limit angle, as is shown in FIG. 4, the elastic section of the strap 19 stretches, because the elastic section 26 has a much greater elasticity than the spring elements 17, 18, which are practically unstretched in the flexion as far as the flexion limit angle. The non-elastic stretch-limiting strap 23 extends by the lengths of the elastic section 26 and, when the flexion limit angle is reached according to FIG. 4, begins to be subjected to a tensile load.

If the knee joint, and thus the hinge 14, is flexed further, as is shown in FIG. 5, the stretch-limiting strap 23 prevents further stretching of the elastic section 26 of the strap 19, such that the elasticity required for the flexion is now provided by the stretching of the spring elements 17, 18.

For the guide element, this means that, during flexion from the extended position in FIG. 3 to the position of flexion as far as the flexion limit angle in FIG. 4, the guide element experiences a slight sideways movement in the medial direction, because the elastic section 26 lengthens on account of its high elasticity. During further flexion, the stretch-limiting strap 23 prevents further lengthening of the elastic section 26, such that the guide element 6 is no longer moved sideways and instead maintains its lateral/medial position during further flexion of the knee joint. Accordingly, the strap sections 10, 12 lengthen on account of the stretching of their spring elements 17, 18.

Although the lengthening of the strap sections 10, 12 is described in the illustrative embodiment as being via spring elements 17, 18, this is not a compulsory solution. It is quite possible for the strap sections 10, 12 to be made of an elastic material or for elastic sections, similar to the elastic section 26, to be inserted into the strap sections 10, 12. It is simply important that the resulting elasticity of the strap sections 10, 12 is much less than the elasticity of the elastic section 26, i.e. the elasticity of the laterally directed strap 19. For the function according to the invention, it is essential that it is only or predominantly the laterally directed strap 19 that is stretched, and that the sideways movement of the guide element 6 is then stopped by the stretch-limiting strap 23, such that further sideways movement of the guide element 6, upon further flexion of the hinge 14, no longer leads to sideways movement or any appreciable sideways movement of the guide element.

It will be noted that FIGS. 3 to 5 show the sequence upon flexion of the joint from the extended position in FIG. 3 to the strongly flexed position in FIG. 5. Of course, the illustration and the description of the function also apply to extension of the joint from the flexed position in FIG. 5 to the extended position in FIG. 3, in which case the guiding of the patella by the guide element 6 from the position formed by the flexion limit angle in FIG. 4 to the extended position is particularly important.

The above-defined flexion limit angle, as far as which a lateral movement of the guide element 6 takes place, is an approximately 30° flexion of the knee joint.

The hinge 14 and the rails 11, 13 connected thereto are not essential to the control of the guide element 6 and can therefore also be omitted from the knee orthosis. Their function lies simply in increasing the stability of the knee orthosis to some extent when the strap sections 10, 12 are fastened to the knee orthosis with their free ends in another suitable way, for example by velcro fasteners arranged on the sleeve 1.

The invention claimed is:

1. Knee-joint orthosis for guiding the patella of a patient during the transition from an extended position to a flexed position of the knee joint and vice versa, with a fastening means for fastening to a thigh and a lower leg, with at least one laterally arranged stabilizing element that takes up a flexion of the knee joint and bears on the thigh and lower leg, and with a dimensionally stable guide element that can be held in position by an arrangement of tensioning straps and is arranged to bear laterally on the patella by way of a lateral base part from which medially directed attachments extend proximally and distally of the patella and are secured to strap sections on the orthosis in the area of the thigh and of the lower leg in such a way that a medial tensile force is exerted on the attachments, wherein the strap sections are designed with an elasticity, that a laterally directed elastic strap allowing a sideways movement of the base part is connected to the base part, the elasticity of which strap is greater than the elasticity of the strap sections, and that the elasticities of the medially directed strap sections, on the one hand, and of the laterally directed strap, on the other hand, are chosen such that, during a flexion of the hinge from the extended position, it is the laterally directed strap that first stretches at least quite predominantly, and a stretch limiter, provided for the laterally directed strap, is active at a predefined flexion limit angle of the knee joint, such that, for a greater flexion of the knee hinge, it is the medially directed strap sections that stretch at least predominantly.

2. Knee-joint orthosis according to claim 1, wherein, when the flexion limit angle is exceeded, only the medially directed strap sections still stretch.

3. Knee-joint orthosis according to claim 1, wherein the laterally arranged stabilizing element is formed by a hinge with two rails mounted so as to be rotatable relative to each other via the hinge, of which a thigh rail is connected to and bears on the fastening means on the thigh, and of which a lower leg rail is connected to and bears on the fastening means on the lower leg.

4. Knee-joint orthosis according to one of claim 1, wherein a hinge arranged on the medial aspect is provided with two rails mounted so as to be rotatable relative to each other via the hinge, of which a thigh rail is connected to and bears on the fastening means on the thigh, and of which a lower leg rail is connected to a bears on the fastening means on the lower leg.

5. Knee-joint orthosis according to claim 4, wherein the medially directed strap sections are connected to a spring element held in the associated rail of the medial hinge, and in that the elasticity of the strap sections results from the elasticity of the associated spring element.

6. Knee-joint orthosis according to one of claim 3, wherein the fastening means is formed by a sleeve made of elastic material and designed to be pulled over the thigh and lower leg.

7. Knee-joint orthosis according to one of claim 6, wherein the laterally directed strap is fastened to the sleeve by velcro fasteners.

8. Knee-joint orthosis according to one of claim 1, wherein the laterally directed strap is fastened on the laterally arranged hinge.

9. Knee-joint orthosis according to one of claim 1, wherein the medially directed strap sections are adjustable in length.

10. Knee-joint orthosis according to one of claim 1, wherein the guide element has a raised edge for bearing on a lateral margin of the patella.

11. Knee-joint orthosis according to one of claim 6, wherein the medially directed strap sections are fastened to the sleeve by velcro fasteners.

12. Knee-joint orthosis according to one of claim 1, wherein the medially directed strap sections are connected to an associated rail of the medially arranged hinge.

* * * * *